(12) United States Patent
Huchzermeier et al.

(10) Patent No.: US 7,449,288 B2
(45) Date of Patent: *Nov. 11, 2008

(54) DETECTION OF BOVINE VIRAL DIARRHEA VIRUS IN TISSUE SAMPLES

(75) Inventors: Roy Huchzermeier, Fayetteville, NY (US); Edward Joseph Dubovi, Ithaca, NY (US)

(73) Assignees: Cornell Research Foundation, Inc., Ithaca, NY (US); IDEXX Laboratories, Inc., Westbrook, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/217,240

(22) Filed: Aug. 9, 2002

(65) Prior Publication Data

US 2003/0143573 A1 Jul. 31, 2003

Related U.S. Application Data

(60) Provisional application No. 60/311,213, filed on Aug. 9, 2001.

(51) Int. Cl.
*C12Q 1/70* (2006.01)
*G01N 33/53* (2006.01)
*G01N 33/00* (2006.01)

(52) U.S. Cl. ............................ 435/5; 435/7.1; 435/7.2; 435/7.92; 435/7.93; 435/7.94

(58) Field of Classification Search ...................... 435/5, 435/7.1, 7.2, 7.21, 7.23, 7.92, 7.93, 7.94, 435/7.5, 7.9, 34, 40.51

See application file for complete search history.

(56) References Cited

U.S. PATENT DOCUMENTS

| | | | |
|---|---|---|---|
| 5,620,691 | A | 4/1997 | Wensvoort et al. |
| 5,648,466 | A | 7/1997 | Vandenbergh et al. |
| 5,705,338 | A | 1/1998 | Piran et al. |
| 6,174,667 | B1 * | 1/2001 | Huchzermeier et al. ......... 435/5 |
| 6,455,264 | B1 * | 9/2002 | Baumeister et al. ........... 435/7.1 |
| 2003/0049610 | A1 | 3/2003 | Huchzermeier et al. |

FOREIGN PATENT DOCUMENTS

| | | |
|---|---|---|
| EP | 0 236 977 | 9/1987 |
| EP | 0 518 756 | 12/1992 |
| WO | 03062785 A2 | 7/2003 |

OTHER PUBLICATIONS

Njaa et al. Journal of Veterinary Diagnostic Investigation. Sep. 2000; 12 (5): 393-399.*
Ellis J. Comparison of detection methods for bovine viral diarrhea virus in bovine abortions and neonatal death. Journal of Veterinary Diagnostic Investigation. Oct. 1995, vol. 7(4), pp. 433-436. Abstract only.*
Grellner W. Quantitative analysis of proinflammatory cytokines in human skin wounds. Forensic Science International 2000, vol. 113, pp. 251-264.*
Helenius A. "Properties of Detergents." in Methods in Enzymology (Academic Press, Inc., 1979), vol. LVI, p. 734-749.*
Neugebauer J. "Detergents: An Overview." in Methods in Enzymology (Academic Press, Inc., 1990), vol. 182, p. 239-253.*
Strickley R. Solubilizing Excipients in Oral and Injectable Formulations, Pharmaceutical Research Feb. 2004, vol. 21, No. 2, p. 201-230.*
Santin et al. Collagen-Bound alpha1-Microglobulin in Normal and Healed Tissues and its Effect on Immunocompetent Cells. Scandinavian Journal of Immunology 1999, vol. 50, p. 289-295.*
Stohlman et al. Isolation of the Dengue Virus Envelope Glycoprotein from Membranes of Infected Cells by Concanavalin A affinity Chromatography. Journal Of Virology, Apr. 1976, vol. 18, No. 1, p. 132-140.*
Mack et al. Cell-free Fatty Acylation of Microsomal Integrated anDde tergentsolubilized Glycoprotein of Vesicular Stomatitis Virus. The Journal of Biological Chemistry 1987, vol. 262, No. 9, Issue of Mar. 25, pp. 4297-4302.*
Payne et al. The polypeptide composition of vaccinia-infected cell membranes and rifampicin bodies. Virus Research Aug.1990, vol. 17, Issue No. 1, p. 15-30. Abstract only.*
Brock et al., "Impact of Bovine Viral Diarrhea Virus on Reproductive Performance," pp. 108-109 (1996).
Brownlie, "Pathogenesis of Mucosal Disease and Molecular Aspects of Bovine Virus Diarrhoea Virus," *Vet. Miccrobiol.*, 23:371-382 (1990).
Brownlie, "Clinical Aspects of the Bovine Virus Diarrhoea/Mucosal Disease Complex in Cattle," *Farm Pract.*, 7:195-202 (1985).
Brownlie, "Variation in Acute Bovine Virus Diarhoea Virus Infections," pp. 176-181 (1996).
Corapi et al., "Monoclonal Antibody Analyses of Cytopathic and Noncytopathic Viruses from Fatal Bovine Viral Diarrhea Virus Infections," *J. Virology*, 62(8):2823-2827 (1988).
Corapi et al., "Characterization of a Panel of Monoclonal Antibodies and Their Use in the Study of the Antigenic Diversity of Bovine Viral Diarrhea Virus," *Am. J. Vet. Res.*, 51(9):1388-1394 (1990).
Donis et al., "Glycoproteins of Bovine Viral Diarrhoea-Mucosal Disease Virus in Infected Bovine Cells," *J. Gen. Virol.*, 68:1607-1616 (1987).
Donis et al., "Characterization of Bovine Viral Diarrhoea-Mucosal Disease Virus-Specific Proteins in Bovine Cells," *J. Gen. Virol.*, 68:1597-1605 (1987).
Dubovi, "Molecular Biology of Bovine Virus Diarrhoea Virus," *Rev. sci. tech. Off. int. Epiz.*, 9(1):105-114 (1990).
Evermann et al., "Clinical Epidemiology of Bovine Viral Diarrhea Virus in the Northwestern United States," p. 193 (1996).
Greiser-Wilke et al., "Immunofluorescence Studies of Biotype-Specific Expression of Bovine Viral Diarrhoea Virus Epitopes in Infected Cells," *J. Gen. Virol.*, 72:2015-2019 (1991).
Homer et al., "Comparison of an Antigen Capture Enzyme-Linked Assay with Reverse Transcription—Polymerase Chain Reaction and Cell Culture Immunoperoxidase Tests for the Diagnosis of Ruminant Pestivirus Infections," *Vet. Microbiol.*, 43:75-84 (1995).

(Continued)

*Primary Examiner*—Bruce Campell
*Assistant Examiner*—Louise Humphrey
(74) *Attorney, Agent, or Firm*—Nixon Peabody LLP

(57) ABSTRACT

The present invention relates to a method of detecting whether a target animal is Bovine Viral Diarrhea Virus (BVDV) positive or negative by determining whether a gp48 protein-specific reagent binds to a gp48 Bovine Viral Diarrhea Virus protein or protein fragment, which retains antigenic specificity, from a target animal's tissue sample.

30 Claims, No Drawings

OTHER PUBLICATIONS

Kwang et al., "Recombinant Polypeptide from the gp48 Region of the Bovine Viral Diarrhea Virus (BVDV) Detects Serum Antibodies in Vaccinated and Infected Cattle," *Vet. Microbiol.*, 32:281-292 (1992).

Meyers et al., "Origin and Diversity of Cytopathogenic Pestiviruses," pp. 24-35 (1996).

Moennig, "Pestiviruses: A Review," *Vet. Microbiol.*, 23:35-54 (1990).

Palfi et al., "Studies on the Decline of Bovine Virus Diarrhoea Virus (BVDV) Maternal Antibodies and Detectability of BVDV in Persistently Infected Calves," *Acta vet. scand.*, 34:105-107 (1993)v.

Paton et al., "Antigenic Variation Amongst Pestiviruses," pp. 61-64 (1996).

Paton et al., "Borders Disease Virus: Delineation by Monoclonal Antibodies," *Arch. Virol.*, 135:241-252 (1994).

Radostits et al., "New Concepts in the Pathogenesis, Diagnosis and Control of Diseases Caused by the Bovine Viral Diarrhea Virus," *Can. Vet. J.*, 29:513-528 (1988).

Rūmenapf et al., "Processing of the Envelope Glycoproteins of Pestiviruses," *J. Virol.*, 67(6):3288-3294 (1993).

Saliki, "Bovine Viral Diarrhea: Clinical Picture in South Central United States," pp. 159-166 (1996).

Shannon et al., "An Antigen-Capture ELISA Detects Pestivirus Antigens in Blood and Tissues of Immunotolerant Carrier Cattle," *J. Virological Methods*, 34:1-12 (1991).

Silva-Krott et al., "Cloning, Sequencing, and in vitro Expression of Glycoprotein gp48 of a Noncytopathogenic Strain of Bovine Viral Diarrhea Virus," *Vet. Microbiol.*, 39:1-14 (1994).

Stark et al., "Genomic Localization of Hog Cholera Virus Glycoproteins," *Virology*, 174:286-289 (1990).

Thiel et al., "Pestivirus Proteins and Vaccination," pp. 112-120 (1996).

Van Rijn et al., "Subdivision of Pestiviruses Based on Genetic and Antigenic Variation of Glycoprotein E2 (GP53)," pp. 206 (1996).

Westaway et al., "Togaviridae," *Intervirology*, 24:125-139 (1985).

Saliki et al., "Microtiter Virus Isolation and Enzyme Immunoassays for Detection of Bovine Viral Diarrhea Virus in Cattle Serum," *J. Clin. Microbiol.*, 35(4):803-807 (1997).

Meyling, "Detection of BVD Virus in Viremic Cattle by an Indirect Immunopeorxidase Technique," in McNulty eds., *Recent Advances in Virus Diagnosis*, Martinus Nijhoff Publishers, Boston, Massachussets, p. 37-46 (1984).

Bezek, "Induction of Thrombocytope nia With Bovine Viral Diarrhea Virus in Acutely and Persistently Infected Cattle," Ph.D. Thesis, Catalogued at Cornell University (1992).

Entrican et al., "A Double Monoclonal Antibody ELISA for Detecting Pestivirus Antigen in the Blood of Viraemic Cattle and Sheep," *Vet. Microbiol.*, 43:65-74 (1995).

Gottschalk et al., "An Antigen Capture Test for the Detection of Cattle Viremic with Bovine Viral Diarrhoea Virus—A Comparison with BVD Virus Isolation from Buffy Coat Cells in Bovine Kidney Cells," *J. Vet. Med.* B 39:467-472 (1992).

Mignon et al., "A Monoclonal ELISA for Bovine Viral Diarrhoea Pestivirus Antigen Detection in Persistently Infected Cattle," *J. Virological Methods*, 35:177-188 (1991).

Haines et al., "Monoclonal Antibody-Based Immunohistochemical Detection of Bovine Viral Diarrhea Virus in Formalin-Fixed, Paraffin-Embedded Tissues," *Vet. Pathol.*, 29:27-32 (1992).

Alkan et al., "Chemiluminescent and Enzyme-Linked Immunoassays for Sensitive Detection of Human IFN-γ" *J. Immunoassay*, 15(3):217-238 (1994).

Waris et al., "Time-Resolved Fluoroimmunoassay Compared with Virus Isolation for Rapid Detection of Respiratory Syncytial Virus in Nasopharyngeal Aspirates," *J. Clin. Microbiol.*, 26(12):2581-2585 (1988).

Baszler et al., "Diagnosis of Naturally Occurring Bovine Viral Diarrhea Virus Infections in Ruminants Using Monoclonal Antibody-Based Immunohistochemistry," *Vet. Pathol.*, 32:609-618 (1995).

Böttcher et al., "Diagnosis of Bovine Virus Diarrhoea by Two Enzyme-Linked Immunosorbent Assays," *Rev. Sci. Tech. Off. Int. Epiz.* 12(2):461-469 (1993).

Saliki et al., "Evaluation of a New Sandwich ELISA Kit That Uses Serum for Detection of Cattle Persistently Infected with BVD Virus," *Annal New York Academy of Sciences* 916:358-363 (2000).

Chimeno Zoth et al., "Expresión y caracterización de dos proteínas estructurales del virus de la diarrea viral bovina (VDVB)," *Revista Argentina de Microbiologia* 33:15-21 (2001), Abstract only in English.

Plavsic et al., "Evaluation of a New Sandwich Enzyme-Linked Immunosorbent Assay for Detection of Bovine Viral Diarrhea Virus in Unprocessed Fetal Bovine Serum," *J. Vet. Diagn. Invest.* 13:261-262 (2001).

Boxman et al., "Detection of Human Papillomavirus Types 6 and 11 in Pubic and Perianal Hair from Patients with Genital Warts," J. of Clinical Microbiology, 37(7):2270-2273 (1999).

Haasnoot et al., "A Fast Immunoawway for the Screening of Beta-agonists in Hair," Analyst 123:2707-2710 (1998).

\* cited by examiner

DETECTION OF BOVINE VIRAL DIARRHEA VIRUS IN TISSUE SAMPLES

This application claims the benefit of U.S. Provisional Patent Application Ser. No. 60/311,213, filed on Aug. 9, 2001.

FIELD OF THE INVENTION

The present invention relates to the detection of Bovine Viral Diarrhea Virus infection in tissue samples from animals.

BACKGROUND OF THE INVENTION

Bovine viral diarrhea virus ("BVDV") currently represents a major threat to the cattle industry. First described over fifty years ago, this pathogen has been found to be both highly virulent and easily spread. Considered a primary pathogen of the bovine enteric, respiratory, reproductive, and immune systems, BVDV continues to cause significant economic losses to the cattle industry worldwide. Recent outbreaks have occurred in Canada, the United States, and throughout the world.

Classified as a member of the genus Pestivirus and Flaviviridae family, BVDV is closely related to sheep border disease virus ("BDV"), and hog cholera virus ("HCV"), both of which are serologically related pestiviruses. Entire or partial genomic sequencing of pestivirus isolates has allowed the determination that a high degree of sequence conservation is present among the pestiviruses. More recently, antigenic variants of BVDV have been identified, and BVDV strains have been divided into two distinct genotypes, type 1 and type 2, which have been further subdivided, based upon cytopathogenicity. Molecular cloning, and polymerase chain reaction (PCR) technology have determined that the general structure of BVDV consists of a capsid protein and three envelope glycoproteins. The genome of BVDV is a 12.3 kb RNA consisting of a single open reading frame ("ORF"). The BVD virus is itself a small, enveloped RNA virus with positive strand polarity. This positive strand aspect of the viral genome allows the RNA to be infectious, even in the absence of virion proteins.

BVDV is spread through a herd in a fecal-oral manner, attacking the enteric, respiratory, reproductive, and immune systems. The viral load needed to provoke symptomatic infection is correlated with the type and strain of BVD virus. In addition, BVDV has the ability to infect fetuses by crossing the placenta, often resulting in a spontaneous abortion of the fetus, and a resultant decreased fertility among infected animals. Strategies for control of BVDV range from stricter management practices in an effort to simply reduce economic loss, to elaborate testing procedures to identify infected animals that, while effective, entail an unacceptable level of cost. Failure of field vaccinations for BVDV has increased the need for a test protocol that will help identify and eliminate infected animals in a cost-effective way.

It should also be noted that BVDV, like other infectious disease agents, is associated with a wide variety of clinical manifestations, creating a very difficult diagnostic challenge. Common manifestations of BVDV infection can include: abortion storms, infertility, irregular heat cycles, early embryonic deaths, fetal mummification, immuno-suppression, dysentery, thrombocytopenia, and cerebral hypoplasia. Moreover, serological studies have shown that a high percentage of cattle infected with BVDV, including those considered to be persistently infected (PI), remain clinically asymptomatic. Such conditions make it imperative that a reliable, inexpensive, and easy-to-use test be developed to assist in the detection of BVDV-infected animals in cattle herds.

The BVD virus is typically maintained in a herd due to the presence of immuno-tolerant PI carrier animals. These PI cattle are exposed to the virus in utero, but can remain clinically asymptomatic throughout the course of their lives, continually shedding fecal matter and bodily fluids with a high concentration of virus, and thereby posing the threat of infection for other animals as long as they remain in the herd. The virus may be present in more than half of the cattle in a herd before signs of an outbreak exhibit themselves. Symptoms of the disease are usually preceded by leukopenia, and testing efforts to date have focused on identifying this effect.

Prior outbreaks of BVDV have resulted in crippling economic losses to the livestock industry. For example, in Ontario in 1993, BVDV cases increased 23% in less than one year. It should also be noted that although the historical assignment of BVDV as a pestivirus was through the species it was first found to be associated with (e.g. cattle), it is now known that pestiviruses can cross species barriers. This indicates that in areas in which wild, free-ranging ruminants (e.g., moose, buffalo, etc.) are exposed to infected cattle herds, these animals are also susceptible to infection from BVDV, or can alternatively act as a reservoir of virus capable of infecting a previously "clean" herd.

Over one hundred and fifty vaccines for BVDV have been marketed to cattle farmers over the past thirty years. These vaccines have consisted of modified live BVD virus or inactivated attenuated virus and virus particles. Recent BVDV outbreaks have occurred, despite the availability and use of these vaccines. Current approaches to vaccination involve repeated yearly inoculation with vaccine for cattle, and additional steps are generally taken in an attempt to insure that no calves are born as PI carriers. However, for effective control of the BVD virus to be possible, it is essential to identify the PI animals and remove them from the herd. Several different test methods have been developed for the detection of BVDV, and/or the detection of BVDV-infected animals. These test methods include: reverse transcription-polymerase chain reaction, enzyme-linked immunoassay (ELISA), standard virus isolation techniques, and immunohistochemistry (Haines et al., "Monoclonal Antibody-Based Immunohistochemical Detection of Bovine Viral Diarrhea Virus in Formalin-Fixed, Paraffin-Embedded Tissues," Vet. Pathol., 29:27-32 (1992)).

Both PCR and virus isolation techniques, owing to their inherent sensitivity, are each capable of detecting very low levels of BVDV. However, these methods are also time-consuming, relatively complex, and expensive. Immunohistochemistry on tissue samples, such as ear notch biopsy samples, is an effective technique for detecting PI animals. This technique, however, is time consuming, labor intensive, and requires highly trained technicians. ELISA technology, although somewhat less sensitive, is better suited as a broad-based diagnostic tool for detecting BVDV infection in animals, because it is cost effective, yields results in a short period of time, and does not require highly trained technicians and a highly specialized laboratory facility. However, antigen-capture ELISA tests for BVDV have historically relied on the use of white blood cell extracts from the animal to be tested. White blood cell extracts have been necessary because BVDV proteins accumulate to relatively high concentrations within the white blood cells of infected animals, and the previous ELISA methods lacked the sensitivity to detect their target BVDV proteins in blood serum (Horner et al., "Comparison of an Antigen Capture Enzyme-Linked Assay with Reverse Transcription-Polymerase Chain Reaction and Cell Culture Immunoperoxidase Tests for the Diagnosis of Ruminant Pestivirus Infections," Vet. Microbiol., 43:75-84 (1995)). The preparation of white cell extracts is itself time consuming and relatively expensive, making any ELISA test reliant upon this extraction costly in and of itself.

Because the above-mentioned methods for detecting BVDV infection in animals are not only time-consuming but often require sophisticated laboratory facilities and highly trained technicians to complete, they are economically prohibitive to use in the broad fashion that is required for today's cattle industry.

More recently, a faster and more cost-effective ELISA test which detects BVDV from serum, plasma, milk, urine, or mucosal fluid samples by using a monoclonal antibody specific for BVDV viral proteins or protein fragments has been developed. See U.S. Pat. No. 6,174,667 and WO 99/15900 to Huchzermeier et al. While this method represents an advance over previously available methods, the serum samples or other bodily fluids may be difficult to collect and/or handle.

The present invention is directed to overcoming the above deficiencies in the art.

SUMMARY OF THE INVENTION

The present invention relates to a method of detecting whether a target animal is Bovine Viral Diarrhea Virus positive or negative. This method involves providing a tissue sample from the target animal. An assay system is provided which includes: (1) a capture antibody that is a Bovine Viral Diarrhea Virus epitope specific antibody, where the capture antibody is immobilized on a solid support and is capable of recognizing and binding a gp48 Bovine Viral Diarrhea Virus protein or protein fragment thereof which retains antigenic specificity; (2) a detector antibody that is an anti-Bovine Viral Diarrhea Virus antibody, capable of recognizing and binding the gp48 Bovine Viral Diarrhea Virus protein or protein fragment thereof which retains antigenic specificity; and (3) a signal generator for indicating the presence of the detector antibody operatively associated with Bovine Viral Diarrhea Virus antigen. The sample is analyzed with the assay system to generate a change in signal if Bovine Viral Diarrhea Virus antigen is present in the sample. The signal is compared to one or more reference levels to indicate whether the target animal is Bovine Viral Diarrhea Virus positive or negative.

The present invention also relates to a method of detecting Bovine Viral Diarrhea Virus infection in a bovine. This method involves providing a tissue sample from the bovine, contacting the sample with a gp48 Bovine Viral Diarrhea Virus protein-specific reagent, and analyzing whether the gp48 Bovine Viral Diarrhea Virus protein-specific reagent binds to a gp48 Bovine Viral Diarrhea Virus protein or protein fragment thereof, which retains antigenic specificity, from the sample.

The traditional method of detecting BVDV-infected animals, including persistently infected (PI) carriers, has been through the use of virus isolation procedures. Immunoassays to detect BVD viral antigen, however, represent an alternative, cost-effective means of detecting BVDV infection, are capable of yielding results in a short period of time (minutes or hours, for example), and do not require highly trained technicians and a highly specialized laboratory facility.

Antigen-capture immunoassays for the detection of BVDV antigens have used predominantly blood samples, either white blood cell extracts, which typically require a time consuming and labor intensive sample preparation procedure, or, more recently, serum. BVD virus and BVDV antigens are ubiquitous throughout the body of an infected animal, particularly a PI carrier animal, and, therefore, can also be isolated from a variety of tissues within the animal. Antigen-capture immunoassays for the detection of BVDV antigen in tissue samples have utilized the P80 viral antigen as the target, and have utilized a lengthy sample preparation procedure to isolate and solubilize the P80 viral antigen from the tissue samples. The P80 viral antigen was the target antigen of choice, because it was known to be present at concentrations high enough to be detectable by immunoassay within the cells of BVDV-infected animals. Previous tissue methods have involved treating the sample with a buffer containing a cell lysing agent, typically a detergent such as NP-40, followed by incubation for approximately 2 hours, and, then, one or two centrifugations to clarify the extract.

In contrast, the present invention utilizes an antigen capture immunoassay specific for the gp48 viral antigen and a much faster and simpler procedure to isolate and solubilize the viral antigen which does not require treatment of the sample with a cell lysing agent. Therefore, the present invention represents a faster, simpler, and more cost-effective means of testing tissue samples and the first reported means of testing cells scraped from the skin for BVDV antigen to detect BVDV-infected animals.

Previous immunoassay methods utilizing blood or serum could not be reliably used to test young animals less than 3 months of age because of potential interference from maternal antibodies. In contrast, the present invention can be used on certain types of tissue sample (e.g. ear notch biopsy and skin scraping) as a reliable means of testing young animals less than 3 months of age for the presence of BVDV. These samples contain the BVDV antigen but do not contain sufficient levels of maternal antibody to interfere with the test.

The method of the present invention has enhanced reliability compared to prior ELISA tests and reveals excellent agreement when compared with the conventional, and established reference methods of BVDV detection—viral isolation and immunohistochemistry. The method of the present invention is easy to use, reliable, quick, and cost effective. In addition, the method of the present invention will aid veterinarians in their efforts to identify BVDV-infected animals, especially PI animals, and remove them from a given herd. This, in turn, protects the cattle industry from significant economic loss due to BVDV. Since BVDV can affect other ruminants, this method can be used on wild animal populations (e.g. deer, moose, elk) to determine if they are BVDV positive. As a result, wild animal populations can be managed to assist in the removal of reservoirs of BVDV virus outside the domestic cattle population.

DETAILED DESCRIPTION OF THE INVENTION

The present invention relates to a method of detecting whether a target animal is Bovine Viral Diarrhea Virus positive or negative. This method involves providing a tissue sample from the target animal. An assay system is provided which includes: (1) a capture antibody that is a Bovine Viral Diarrhea Virus epitope specific antibody, where the capture antibody is immobilized on a solid support and is capable of recognizing and binding a gp48 Bovine Viral Diarrhea Virus protein or protein fragment thereof which retains antigenic specificity; (2) a detector antibody that is an anti-Bovine Viral Diarrhea Virus antibody, capable of recognizing and binding the gp48 Bovine Viral Diarrhea Virus protein or protein fragment thereof which retains antigenic specificity; and (3) a signal generator for indicating the presence of the detector antibody operatively associated with Bovine Viral Diarrhea Virus antigen. The sample is analyzed with the assay system to generate a change in signal if Bovine Viral Diarrhea Virus antigen is present in the sample. The signal is compared to one or more reference levels to indicate whether the target animal is Bovine Viral Diarrhea Virus positive or negative.

The present invention also relates to a method of detecting Bovine Viral Diarrhea Virus infection in a bovine. This method involves providing a tissue sample from the bovine, contacting the sample with a gp48 Bovine Viral Diarrhea Virus protein-specific reagent, and analyzing whether the gp48 Bovine Viral Diarrhea Virus protein-specific reagent binds to a gp48 Bovine Viral Diarrhea Virus protein or protein fragment thereof, which retains antigenic specificity, from the sample.

The present invention can be carried out with a polyclonal antibody or a monoclonal antibody.

Monoclonal antibody production may be affected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature,* 256:495 (1975), which is hereby incorporated by reference in its entirety.

The immune lymphocytes are produced by in vivo immunization of the animal (e.g., a mouse) with the protein or polypeptide of interest. Such immunizations are repeated as necessary at intervals of up to several weeks to obtain a sufficient titer of antibodies. Following the last antigen boost, the animals are sacrificed and the spleen cells are removed.

Fusion with mammalian mycloma cells or other fusion partners capable of replicating indefinitely in cell culture is effected by standard and well-known techniques, for example, by using polyethylene glycol (PEG) or other fusing agents. See Milstein and Kohler, *Eur. J. Immunol.,* 6:511 (1976), which is hereby incorporated by reference in its entirety. This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering the protein or polypeptide of interest subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in Harlow et al. (eds), *Antibodies: A Laboratory Manual* (1988), which is hereby incorporated by reference in its entirety.

After the antibodies are prepared, they can be labeled with radiolabels, fluorescent labels such as fluorescein and rhodamine, nuclear magnetic resonance active labels, chemiluminescers such as luciferin, and enzymatic markers such as peroxidase or phosphatase. The antibody can be labeled with such reagents using techniques known in the art. For example, see Wensel and Meares, *Radioimmunoimaging and Radioimmunotherapy,* Elsevier, N.Y. (1983), which is hereby incorporated by reference in its entirety, for techniques relating to the radiolabeling of antibodies. See also Colcher et al., "Use of Monoclonal Antibodies as Radiopharmaceuticals for the Localization of Human Carcinoma Xenografts in Athymic Mice," *Meth. Enzymol.,* 121: 802-816 (1986), which is hereby incorporated by reference in its entirety.

BVDV-infected animals have previously been identified by testing their blood samples using a virus isolation procedure, which can only be performed by highly trained technicians in a highly specialized laboratory facility. Recently, as an alternative means of detecting BVDV antigen in infected animals, antigen capture immunoassays for serum or other bodily fluid samples which utilizes the BVDV antigen specific monoclonal antibody, 15.c.5, have been developed, as described in U.S. Pat. No. 6,174,667 to Huchzermeier et al., which is hereby incorporated by reference in its entirety. The 15.c.5 monoclonal antibody recognizes an epitope of the BVDV gp48 (alternatively known as "EO" or "$E^{rns}$") glycoprotein (Corapi et al., "Monoclonal Antibody Analysis of Cytopathic and Noncytopathic Viruses from Fatal Bovine Viral Diarrhea Virus Infections," *J. Virol.,* 62(8): 2823-2827 (1988), which is hereby incorporated by reference in its entirety) and a mouse hybridoma known as BVD MAB 15.C.5 has been deposited with the American Type Culture Collection, now at 10801 University Boulevard, Manassas, Va. 20110-2209 under ATCC Accession No. PTA-716.

The present invention preferably utilizes an antigen capture immunoassay for tissue samples and skin scrapings which employs the 15.c.5 monoclonal antibody and involves a simpler, faster, and less expensive sample preparation procedure than conventional BVDV detection techniques.

In certain embodiments of the present invention, the tissue from the target animal can be skin biopsy tissue or skin scrapings. Tissue taken from lymph mode or spleen can also be used.

A convenient method of obtaining a suitable tissue for BVDV testing is to cut an approximate piece of 1 $cm^2$-size tissue from the edge of an animal's ear. There are commercially available ear notching tools that can be utilized for this purpose. Pieces of tissue that are routinely removed from animals for other purposes are also suitable for BVDV testing (e.g. tail clippings).

Another convenient method of obtaining a suitable tissue for BVDV testing is to scrape cells from the surface of an animal's skin. This can be accomplished by repeatedly scraping the surface of the skin with a blunt spatula-like tool (e.g. wooden applicator stick). Alternatively, a cotton swab can be repeatedly rubbed over the animal's skin.

The tissue sample can be provided by suspending the tissue in a solvent such as a diluent buffer that contains no cell lysing agents (such as detergents) to solubilize any gp48 BVDV protein or fragment thereof. The supernatant is then assayed for the presence of the gp48 viral antigen. The volume of the sample required for purposes of this assay system is at least 100 μl per well. The method of the present invention can be used on young calves, which is an advantage over the serum ELISA.

The assay system of the present invention preferably employs a BVDV antigen specific monoclonal antibody as the capture antibody, with a goat polyclonal anti-BVDV antibody as the detector antibody and a horseradish peroxidase-anti-goat antibody as the conjugate. The test results may be determined through the use of a microplate spectrophotometer wherein an optical density is read at 450 nanometers.

The BVDV tissue immunoassay can be either a sandwich type immunoassay, employing a gp48 specific antibody (as a capture or detector antibody) and another gp48 specific antibody (as a detector or capture antibody to complement the first gp48 specific antibody), or a competitive type immunoassay, employing a gp48 specific antibody with a labeled gp48 antigen or gp48 antigen attached to a solid phase.

A variety of configurations and formats are possible for each type of immunoassay. The capture antibody, for example, can be attached to a variety of different solid phases to enable the washing away of unreacted assay reagents during the course of the assay. These include: microwells, coated test tubes, coated magnetic particles, wands or sticks, and membranes (nitrocellulose and others).

The capture antibody, also referred to as primary antibody, can be attached by passive adsorption, covalent coupling, or by using a solid phase pre-coated with a secondary binder such as protein A, protein G, a secondary antibody specific for the primary antibody, avidin, or an antibody specific for a particular ligand (i.e.: biotin, dinitrophenol, fluorescein, and others). In the case of avidin or any of the ligand specific antibodies, it is necessary to covalently attach the ligand to the capture antibody.

For a competitive type assay, the gp48 antigen can be attached to a solid phase by passive adsorption, covalent coupling, or by using a solid phase pre-coated with a secondary binder such as avidin an antibody specific for a particular ligand such as dinitrophenol, fluorescein and others. In the case of avidin or any of the ligand specific antibodies, it is necessary to covalently attach the ligand to the gp48 antigen.

A variety of labels (signal generators) can be employed in sandwich or competitive type immunoassays, including: enzymes such as peroxidase, horseradish peroxidase, or alkaline phosphatase; fluorophores such as fluorescein and rhodamine; chemiluminescent probes such as an acridinium ester or luciferin; a time-resolved probe such as an europium chelate; radioactive species such as $^{14}C$, $^{3}H$, $^{35}S$ $^{125}I$, $^{32}P$, or $^{131}I$; or particles such as colloidal gold, plain latex, or dyed latex.

Procedures for labeling antibodies with radioactive isotopes are generally known in the art. Tritium labeling procedures are described in U.S. Pat. No. 4,302,438, which is hereby incorporated by reference in its entirety. Iodinating, tritium labeling, and $^{35}S$ labeling procedures especially adapted for murine monoclonal antibodies are described by Goding, *Monoclonal Antibodies: Principles and Practice*, pp. 124-126, N.Y. Academic Press (1983) and the references cited therein, which are hereby incorporated by reference in their entirety. Other procedures for iodinating antibodies are described by Hunter and Greenwood, *Nature*, 144:945 (1962); David et al., *Biochemistry*, 13:1014-1021 (1974), and U.S. Pat. Nos. 3,867,517 and 4,376,110, which are hereby incorporated by reference in their entirety.

Fluorophore and chromphore labeled antibodies can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science*, 162:526 (1968) and Brand et al., *Annual Review of Biochemistry*, 41:843-868 (1972), which are hereby incorporated by reference in their entirety. The antibodies can be labeled with fluorescent chromophore groups by conventional procedures such as those disclosed in U.S. Pat. Nos. 3,940,475, 4,289,747, and 4,376,110, which are hereby incorporated by reference in their entirety.

One group of fluorescers having a number of the desirable properties described above are the xanthene dyes, which include the fluoresceins derived from 3,6-dihydroxy-9-henylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Antibodies can be labeled with fluorchromes or chromophores by the procedures described by Goding, *Monoclonal Antibodies: Principles and Practice*, pp. 208-249, N.Y. Academic Press (1983).

The gp48 specific monoclonal antibody or the anti-BVDV antibody can be either directly labeled by covalent coupling or a labeled secondary antibody that is specific for the corresponding primary antibody and can be used without the need to chemically modify the primary antibody. A labeled secondary binder such as avidin or a labeled antibody specific for a particular ligand (i.e. dinitrophenol, fluorescein, and others) can also be employed. In the case of avidin or any of the ligand specific antibodies, it is necessary to covalently attach the corresponding ligand to the primary antibody.

For a competitive type assay, the gp48 antigen can be labeled directly by covalent coupling or a labeled secondary binder such as avidin or a labeled antibody specific for a particular ligand (i.e. dinitrophenol, fluorescein, and others) can be employed. In the case of avidin or any of the ligand specific antibodies, it is necessary to covalently attach the corresponding ligand to the gp48 antigen.

In another embodiment of the present invention, the assay system includes a quantity of the capture antibody sufficient to optimize the detection of the gp48 BVDV protein or the protein fragment from the sample taken from the target animal. In addition, the concentration of detector antibody, the particular anti-goat conjugate and its concentration, the formulation of the reagent diluent buffer, the formulation of the non-specific binding (NSB) reagent, and the type of microwell can all be optimized to yield the lowest background and highest signal-to-noise ratio. Furthermore, the reagent configuration (i.e. 10× concentrates of detector reagent, enzyme conjugate reagent and NSB reagent, with a separate reagent diluent buffer) can be designed to maximize kit stability and shelf life.

A small amount of bovine gamma globulin can be added to the reagent diluent buffer used to prepare working solutions of detector antibody and enzyme conjugate. As a result, the background signal is significantly reduced.

In addition, it is advantageous to utilize a purified monoclonal antibody rather than a crude ascites preparation for well coating to insure consistency between batches of coated microplates. The problem of high background signal when purified 15.c.5 is coated onto wells can be alleviated by the addition of bovine albumin to the purified 15.c.5 prior to well coating.

The ELISA procedure is carried out at room temperature and takes approximately 4 hours to complete, though it does not require highly specialized laboratory facilities.

With regard to the components of the test kit, each kit contains one negative control and one positive control. These controls are included within each run to insure that each run is valid and to be used in the data reduction calculation (to "normalize" the sample results). These controls, as well as all the other reagents used in the assay are preserved with the addition of Thimerosal.

To minimize the necessary container volumes and maximize kit stability, the detector reagent, enzyme conjugate reagent, non-specific binding inhibiting reagent (e.g. the "NSB" reagent), and the ELISA wash buffer can be supplied as 10× concentrates. The reagent diluent buffer, the negative control, the positive control, the tetramethyl benzidine (TMB) substrate reagent, and a solution that will stop the reaction (the stop solution) can be supplied in the kit in a ready-to-use form with no need for dilution. The samples are run in one of two 96-well plates provided in the kit.

Other compounds or resources needed to perform the BVDV Antigen assay system include among other things: de-ionized water, a microplate reader capable of making an optical density (OD) reading at 450 nm, serological pipets, and precision pipettors.

EXAMPLES

The following examples are provided to illustrate embodiments of the present invention but are by no means intended to limit its scope.

Example 1

Reagent Compositions

The compounds comprising the ELISA Wash Buffer are: 0.1 M Tris HCl (6.25 Normal) for pH adjustment; 0.001% Thimerosal (Sigma Chemical Company, St. Louis, Mo.); and 0.5% Tween 20.

The compounds comprising the Detector Reagent-10× concentrate are: 25% Ethylene Glycol; 0.01% Thimerosal; approximately 5% goat anti-BVD antibody; and 0.06% yellow food coloring in PBS (pH 7.4).

The compounds comprising the NSB Reagent-10× concentrate are: 25% Ethylene Glycol, 0.01% Thimerosal, 0.2% Mouse IgG, and 0.06% red food coloring in PBS (pH 7.4).

The compounds comprising the Reagent Diluent Buffer are: 2.5% Bovine Serum Albumin, 0.01% Thimerosal, 0.625% Igepal CA-630 (Sigma Chemical Company, St. Louis, Mo.), and 2 µg/ml bovine gamma globulin in PBS (pH 7.4).

The tetramethyl benzidine (TMB) substrate is commercially available. Suppliers of this substrate include: BioFX Laboratories (Owings Mills, Md.), Pierce Chemical Co. (Rockford, Ill.), and Kirkegaard & Perry Laboratories (Gaithersburg, Md.).

The stop solution consists of an acidic formulation. It can typically be purchased as a ready-to-use reagent from BioFX Laboratories (Owings Mills, Md.).

Each 96-well tray is coated overnight with 0.1 ml per well of a solution containing the anti-BVDV antibody such as purified 15.c.5 (available through the Diagnostic Laboratory at the College of Veterinary Medicine, Cornell University, Ithaca, N.Y.) at 5 µg/ml and bovine serum albumin at 10 µg/ml in carbonate buffer (pH 9.6). Following the coating, each tray is washed three times with ELISA wash buffer and allowed to dry overnight at 4° C. A foil pouch is used to encase each tray after drying, and a desiccant is included inside each pouch to remove moisture.

The compounds comprising the Enzyme Conjugate Reagent-10× concentrate are: 25% Ethylene Glycol, 0.01% Thimerosal, anti-goat antibody conjugated to detection mechanism, typically horseradish peroxidase (dilution approximately 1 to 700), 0.1% rabbit albumin, and 0.02% rabbit gamma globulin in PBS (pH 7.4).

The compounds comprising the negative control for the assay kit are 1% Igepal CA-630 and 0.01% Thimerosal in PBS (pH 7.4).

The compounds comprising the positive control for the assay kit are 1% Igepal CA-630, 0.01% Thimerosal, 1% Bovine Serum Albumin, BVDV culture (diluted appropriately) and 50 µM phenyl methyl sulfonyl fluoride in PBS (pH 7.4).

Example 2

ELISA Protocol

To run the ELISA, the user should employ the needed number of microwells from one or more of the provided 96-well plates. The microwells themselves can be removed from the plates provided, any excess wells should be saved for future assays. The wells are first pre-wetted by pipetting 0.2 ml of ELISA Wash Buffer into each well; this buffer should then be removed or poured off the wells prior to the addition of sample. As with each of the wash steps, it is important that all ELISA Wash Buffer added to the wells is removed, while also insuring that the wells do not dry out between steps. Thereafter, 100 µl of sample or control is pipetted into each well.

After addition of the sample or control, cover the wells with self-adhesive transparent film cut to the appropriate size, and incubate the wells at room temperature for 1 to 1.5 hours. The working Detector Reagent should then be prepared by mixing 1 part of the Detector Reagent-10× concentrate, 1 part of NSB Reagent 10× concentrate, and 8 parts of Reagent Diluent Buffer. The Working Detector Reagent should be prepared within approximately 1 hour of anticipated use and stored at 4° C.

After the incubation period, liquid from the wells is removed as described above and the wells are washed by adding 0.2 ml of ELISA Wash Buffer to each well and then removing or pouring off the ELISA Wash Buffer. This wash process should be repeated two more times to yield a total of three washes. After this step, 0.1 ml of working Detector Reagent should be pipetted into each sample and control microwell. The wells are covered with the adhesive film and incubated at room temperature for 1 to 1.5 hours. During this time, the working Enzyme Conjugate Reagent should be prepared by mixing 1 part of enzyme conjugate reagent-10× concentrate, 1 part of NSB Reagent-10× concentrate, and 8 parts of Reagent Diluent Buffer. The Working Enzyme Conjugate Reagent should be prepared within approximately 1 hour of anticipated use and stored at 4° C. After the incubation period, liquid from the wells is removed as described above, and the wells are washed a total of three times as described above. Thereafter, 0.1 ml of working Enzyme Conjugate Reagent is pipetted into each microwell. When this is accomplished, the wells are covered with adhesive film and incubated at room temperature for 1 to 1.5 hours. While this incubation is ongoing, the TMB Substrate Reagent and Stop Solution are retrieved and are allowed to equilibrate at room temperature or remain at room temperature.

After the incubation period, the liquid is removed from the wells and the wells are washed a total of three times, as described above. 0.1 ml of TMB substrate reagent is pipetted into each microwell. To avoid contamination of the TMB substrate, it is recommended that the quantity of TMB to be used be poured out of its bottle into a separate container for pipetting and that any left over TMB be discarded rather than returned to its original container. After the TMB substrate reagent has been put into the wells, the wells are covered and incubated at room temperature in the dark for 10 to 12 minutes. After this incubation period, 0.1 ml of Stop Solution is pipetted into each microwell, and the wells are again incubated at room temperature in the dark for 5 to 10 minutes. Once this final incubation is completed, the absorbance of each well is determined at 450 nm against an air or water blank on a microplate reader or other suitable spectrophotometer.

With regard to the above protocol, it should be noted that to insure the accuracy and quality of results reached, both positive and negative controls should be included in every ELISA run. The BVDV Antigen Test Kit itself should be stored at 2-8° C. in order to maintain its shelf life and effectiveness for as long as possible.

Example 3

ELISA Data Reduction

The data is reduced by first calculating the average raw OD (optical density) for each control and sample assayed. The average OD value obtained for the Negative Control is then subtracted from each of the other average raw OD values to obtain blank-corrected OD values for the corresponding positive control and samples. This step eliminates the background noise (due to non-specific binding of enzyme conjugate) from the specific signal. A "normalized" OD is then calculated for each sample by dividing the blank-corrected OD of that sample by the "blank-corrected" OD of the Positive Control. Normalizing the results in this manner greatly diminishes the run-to-run variation. The normalized OD values thus gained are compared with the following guidelines (Table 1) to determine the BVDV status of the animal.

TABLE 1

Optical Density Chart for the Determination of BVDV Status

| "Normalized" OD Values | BVDV Status |
|---|---|
| Less than 0.20 | BVDV NEGATIVE |
| 0.20 to 0.39 | "Gray Zone" |
| Greater than 0.39 | BVDV POSITIVE |

With regard to the above comparison, if a "Normalized" OD is obtained that is within the "gray zone," the sample should be re-assayed using the standard working reagents as previously used and also assayed without detector antibody in the working detector antibody reagent.

The raw OD obtained without detector should be subtracted from the raw OD obtained with detector; this difference should then be divided by the blanked OD of the positive kit control (the OD of the negative kit control should be used to blank the positive kit control as usual). A new normalized value less than 0.2 should be considered BVDV negative, a new normalized OD value of 0.2 or greater should be considered BVDV-positive.

Example 4

Quality Control

In order to maintain consistently reliable data, raw OD values (e.g., unblanked) obtained for the kit—with regard to the positive and negative controls—should fall within the ranges seen in Table 2.

TABLE 2

Unblanked Optical Density Standards for Reliability

Raw OD Values

| Negative Control | <0.5 |
|---|---|
| Positive Control | >0.8 |

Example 5

BVDV Analysis

Ear notches from 100 animals were tested in the BVDV antigen-capture ELISA (ACE) and the results were compared to reference tests performed on the same animals (virus isolation, PCR, or antigen-capture immunoassay on blood, or immunohistochemistry on a separate fixed ear notch). Thirty-nine of the subject animals were BVDV-positive and sixty-one were BVDV-negative by a reference method. The subject animals ranged in age from 1 day to adult. The correlation between the ear notch/ACE results and the reference results was excellent.

TABLE 3

Comparison of Different BVDV Analysis Methods

| | Ear notch/ACE Results | | |
|---|---|---|---|
| | Positive | Negative | Total |
| Reference Method | | | |
| Positive | 39 | 0 | 39 |
| Negative | 0 | 61 | 61 |
| Total | 39 | 61 | 100 |

Relative sensitivity = 39/39 = 100%
Relative specificity = 61/61 = 100%

Since an acute BVDV infection can result in the production of viral antigens over a short period of time, a BVDV-positive result in the ELISA may not always be indicative of a persistently infected animal. A definitive, diagnosis that a particular animal is persistently infected should only be made after a second sample is taken from the subject animal at least 3 weeks after the initial sample and that second sample is also found to be BVDV-positive.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of detecting whether a target animal is Bovine Viral Diarrhea Virus positive or negative comprising:

a) suspending a tissue sample comprising skin from said target animal in a diluent under conditions effective to solubilize any gp48 Bovine Viral Diarrhea Virus protein or protein fragment thereof without lysing cells;

b) providing an assay system which comprises:

1) a capture antibody that is a Bovine Viral Diarrhea Virus epitope specific antibody, said capture antibody being immobilized on a solid support and capable of recognizing and binding a gp48 Bovine Viral Diarrhea Virus protein or protein fragment thereof which retains antigenic specificity;

2) a detector antibody that is an anti-Bovine Viral Diarrhea Virus antibody, capable of recognizing and binding said gp48 Bovine Viral Diarrhea Virus protein or protein fragment thereof which retains antigenic specificity; and 3) a signal generator for indicating the presence of said detector antibody operatively associated with Bovine Viral Diarrhea Virus antigen;

c) analyzing said diluent in which the tissue sample comprising skin is suspended with said assay system to generate a change in signal if gp48 Bovine Viral Diarrhea Virus antigen which retains its antigenic and epitopic specificity is present in the sample compared to when no such antigen is present; and d) comparing the signal generated to one or more reference levels to indicate whether the target animal is Bovine Viral Diarrhea Virus positive or negative.

2. The method of claim 1, wherein said tissue is skin biopsy tissue.

3. The method of claim 1, wherein said tissue is a skin scraping.

4. The method of claim 1, wherein said assay system includes a quantity of said capture antibody sufficient to optimize the detection of said gp48 Bovine Viral Diarrhea Virus protein or said protein fragment from said sample taken from said target animal.

5. The method of claim 1, wherein said Bovine Viral Diarrhea Virus epitope specific antibody is the monoclonal antibody designated as 15.c.5.

6. The method of claim 1, wherein said capture antibody is a polyclonal antibody.

7. The method of claim 1, wherein said capture antibody is a monoclonal antibody.

8. The method of claim 1, wherein said anti-Bovine Viral Diarrhea Virus detector antibody is a polyclonal antibody.

9. The method of claim 1,wherein said anti-Bovine Viral Diarrhea Virus detector antibody is a monoclonal antibody.

10. The method of claim 1, wherein the signal generator has a marker directly conjugated to said detector antibody.

11. The method of claim 1, wherein said signal generator is selected from the group consisting of: peroxidase, alkaline phosphatase, a fluorophore, a chemiluminescent probe, a time-resolved probe, a radioactive species, particles of colloidal gold, plain latex, horseradish peroxidase, and dyed latex.

12. The method of claim 11, wherein the signal generator is a fluorescein fluorophore.

13. The method of claim 11, wherein the signal generator is an acridinium ester chemiluminescent probe.

14. The method of claim 11, wherein the signal generator is an europium chelate time-resolved probe.

15. A method of detecting Bovine Viral Diarrhea Virus infection in a bovine comprising:

suspending a tissue sample comprising skin from the bovine in a diluent under conditions effective to solubilize any gp48 Bovine Viral Diarrhea Virus protein or protein fragment thereof without lysing cells;

contacting said diluent in which the tissue sample comprising skin is suspended with a gp48 Bovine Viral Diarrhea Virus protein-specific reagent;

analyzing whether the reagent binds to a gp48 Bovine Viral Diarrhea Virus protein or protein fragment thereof from said diluent in which the tissue sample comprising skin is suspended, whereby a change in signal is generated if a Bovine Viral Diarrhea Virus protein or protein fragment, which retains antigenic and epitopic specificity, is present in the sample compared to when no such protein or protein fragment is present; and comparing the signal generated to one or more reference levels to indicate whether the bovine is infected with Bovine Viral Diarrhea Virus.

16. The method according to claim 15, wherein said tissue is skin biopsy tissue.

17. The method according to claim 15, wherein said tissue is a skin scraping.

18. The method according to claim 15, wherein said analyzing is carried out with a polyclonal antibody.

19. The method according to claim 15, wherein said analyzing is carried out with a monoclonal antibody.

20. The method according to claim 19, wherein the monoclonal antibody is 15.c.5.

21. The method according to claim 15, wherein said analyzing is carried out with a sandwich immunoassay.

22. The method according to claim 15, wherein said analyzing is carried out in a competitive immunoassay.

23. The method of claim 2 wherein said skin biopsy tissue is an ear notch.

24. The method of claim 16, wherein said skin biopsy tissue is an ear notch.

25. The method of claim 1, wherein the diluent is a diluent buffer.

26. The method of claim 1, wherein the diluent does not contain any detergent.

27. The method of claim 1, wherein the antigenic and epitopic specificity of the Bovine Viral Diarrhea Virus protein or protein fragment is the epitope of the gp48 glycoprotein recognized by the monoclonal antibody designated as 15.c.5.

28. The method of claim 15, wherein the diluent is a diluent buffer.

29. The method of claim 15, wherein the diluent does not contain any detergent.

30. The method of claim 15, wherein the antigenic and epitopic specificity of the Bovine Viral Diarrhea Virus protein or protein fragment is the epitope of the gp48 glycoprotein recognized by the monoclonal antibody designated as 15.c.5.

* * * * *